(12) United States Patent
Wang et al.

(10) Patent No.: US 10,610,529 B2
(45) Date of Patent: Apr. 7, 2020

(54) TRABECTEDIN-INCLUSIVE INJECTABLE PHARMACEUTICAL COMPOSITION FOR GASTROINTESTINAL EXTERNAL USE AND A METHOD FOR MANUFACTURING THE SAME

(71) Applicant: Jiangsu Hengrui Medicine Co., Ltd., Lianyungang, Jiangsu (CN)

(72) Inventors: Likun Wang, Jiangsu (CN); Qiong Sun, Jiangsu (CN); Chen Xu, Jiangsu (CN); Rong Yin, Jiangsu (CN); Kai Liu, Jiangsu (CN)

(73) Assignee: Jiangsu Hengrui Medicine Co., Ltd., Lianyungang, Jiangsu (CN)

( * ) Notice: Subject to any disclaimer, the term of this patent is extended or adjusted under 35 U.S.C. 154(b) by 0 days.

(21) Appl. No.: 16/072,992

(22) PCT Filed: Jan. 23, 2017

(86) PCT No.: PCT/CN2017/072220
§ 371 (c)(1),
(2) Date: Jul. 26, 2018

(87) PCT Pub. No.: WO2017/133544
PCT Pub. Date: Aug. 10, 2017

(65) Prior Publication Data
US 2019/0030028 A1    Jan. 31, 2019

(30) Foreign Application Priority Data

Feb. 4, 2016 (CN) .......................... 2016 1 0081052

(51) Int. Cl.
| | | |
|---|---|---|
| *A61K 31/4995* | (2006.01) | |
| *A61K 47/10* | (2017.01) | |
| *A61K 47/26* | (2006.01) | |
| *A61K 9/19* | (2006.01) | |
| *A61K 9/00* | (2006.01) | |
| *A61K 47/02* | (2006.01) | |
| *A61K 47/38* | (2006.01) | |
| *A61K 47/40* | (2006.01) | |
| *A61K 47/42* | (2017.01) | |

(52) U.S. Cl.
CPC ........ *A61K 31/4995* (2013.01); *A61K 9/0019* (2013.01); *A61K 9/19* (2013.01); *A61K 47/02* (2013.01); *A61K 47/10* (2013.01); *A61K 47/26* (2013.01); *A61K 47/38* (2013.01); *A61K 47/40* (2013.01); *A61K 47/42* (2013.01)

(58) Field of Classification Search
CPC .... A61K 31/4995; A61K 47/02; A61K 47/10; A61K 47/26; A61K 47/38; A61K 47/40; A61K 47/42; A61K 9/0019; A61K 9/19
See application file for complete search history.

(56) References Cited

U.S. PATENT DOCUMENTS

| 8,895,557 B2 * | 11/2014 | Beijnen | A61K 9/0019 514/249 |
|---|---|---|---|
| 2006/0094687 A1 * | 5/2006 | Beijnen | A61K 9/0019 514/53 |
| 2015/0094313 A1 * | 4/2015 | Beijnen | A61K 9/0019 514/250 |

FOREIGN PATENT DOCUMENTS

| CN | 1360503 A | 7/2002 |
|---|---|---|
| CN | 1823794 A | 8/2006 |
| CN | 102018714 A | 4/2011 |
| WO | 0069441 A1 | 11/2000 |

OTHER PUBLICATIONS

Abdelwahed et al. (Advanced Drug Delivery Reviews, 2006, 1688-1713). (Year: 2006).*
CN1360503, English translation (Year: 2002).*
CN1823794, English translation (Year: 2006).*
Menchaca et al, "Synthesis of Natural Ecteinascidins (ET-729, ET-745, ET-759B, ET-736, ET-637, ET-594) from Cyanosafracin B," Journal of Organic Chemistry, vol. 68, No. 23, pp. 8859-8866 (2003).
Int'l Search Report dated Apr. 28, 2017 in Int'l Application No. PCT/CN2017/072220.

* cited by examiner

*Primary Examiner* — Umamaheswari Ramachandran
(74) *Attorney, Agent, or Firm* — Panitch Schwarze Belisario & Nadel LLP

(57) ABSTRACT

The present invention relates to a trabectedin-inclusive injectable pharmaceutical composition for gastrointestinal external use and a method for manufacturing the same. Specifically, the composition contains trabectedin and a first excipient, the first excipient being selected from one or more of monosaccharide or polylols. The preparation in the present invention has a stable quality, and can be applied to mass production.

18 Claims, 5 Drawing Sheets

TRABECTEDIN-INCLUSIVE INJECTABLE PHARMACEUTICAL COMPOSITION FOR GASTROINTESTINAL EXTERNAL USE AND A METHOD FOR MANUFACTURING THE SAME

CROSS-REFERENCE TO RELATED APPLICATION

This application is a Section 371 of International Application No. PCT/CN2017/072220, filed Jan. 23, 2017, which was published in the Chinese language on Aug. 10, 2017, under International Publication No. WO 2017/133544 A1, which claims priority under 35 U.S.C. § 119(b) to Chinese Application No. 201610081052.5, filed Feb. 4, 2016, the disclosures of which are incorporated herein by reference in their entirety.

FIELD OF THE INVENTION

The present invention relates to an injectable parenteral pharmaceutical formulation of trabectedin and a method for manufacturing the same.

BACKGROUND OF THE INVENTION

Trabectedin (Ecteinascidin-743, ET-743) is a tetrahydroisoquinoline alkaloid initially isolated from a marine organism *Ecteinascidia turbinata*, and now mainly is prepared by chemical synthesis. Trabectedin has a unique and complex mechanism of action. It can inhibit the transcription of heat shock inducing genes, and can also interact with the transcription-coupled nucleoside excision repair system, resulting in the formation of lethal DNA strand. Trabectedin has a strong in vitro activity against multiple tumor cell lines, such as soft tissue sarcoma, leukemia, melanoma, breast cancer, non-small cell lung cancer, and ovarian cancer.

The structure of ET-743 (Formula I) is as follows:

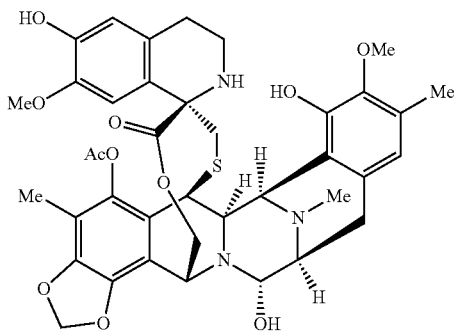

Formula I

ET-743 is a complex compound with a limited solubility in pure water. The solubility of ET-743 in water can be increased by adjusting the pH of the solution to 4. However, ET-743 has a poor thermal stability. It rapidly degrades at room temperature (25° C.), and can only be stored for 1 month when refrigerated at 5° C. Therefore, trabectedin can only be long-term stored at −20° C., which greatly limits the clinical application thereof. Thus, it is necessary to improve the thermal stability of ET-743 by means of pharmaceutics. Meanwhile, it is also a great challenge for those skilled in the art.

The main impurities in trabectedin are ET-701, ET-745, ET-759B and ET-789A (Synthesis of Natural Ecteinascidins (ET-729, ET-745, ET-759B, ET-736, ET-637, ET-594) from Cyanosafracin B, Journal of Organic Chemistry, 2003, 68(23), Page 8859-8866). Among them, the impurity ET-701 is a hydrolysate, and is the main impurity during the processes of lyophilization and storage of the formulation; and the impurity ET-745 is a reduction product of trabectedin. Their structures are as follows:

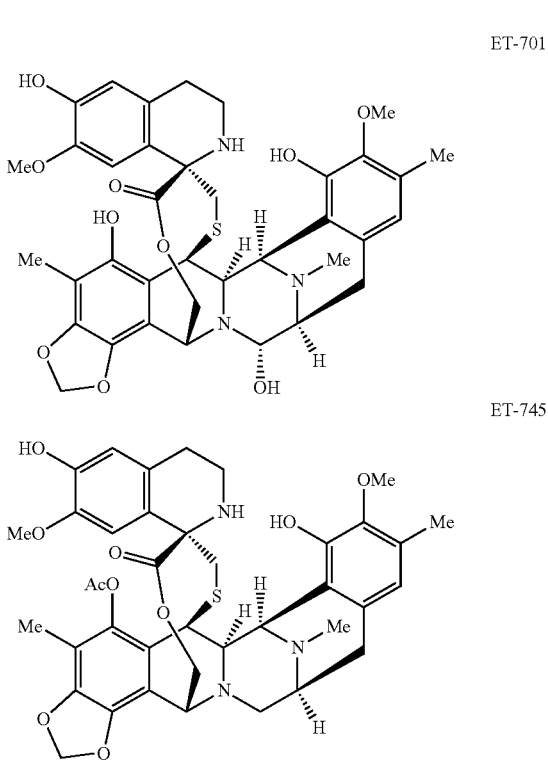

WO 0069441 discloses a sterile lyophilized formulation, comprising ET-743, mannitol and a phosphate buffer. The lyophilized formulation can be used for intravenous injection after being reconstituted and diluted. However, the formulation is not stable for long-term storage under refrigeration or at room temperature. It has to be stored at −15 to −25° C. in the dark. CN102018714A discloses a ET-743 lyophilized formulation, comprising a disaccharide selected from the group consisting of lactose, sucrose, and trehalose. In the study, it was found that these formulations showed the degradation of the active ingredient when stored for 3 months under accelerated conditions of 40°C./70% RH, suggesting that these formulations are still not stable if being stored for a long time. Therefore, it is very necessary to develop a novel and stable ET-743 formulation.

SUMMARY OF THE INVENTION

The present invention provides a stable trabectedin pharmaceutical composition.

Specifically, the present invention provides an injectable parenteral pharmaceutical composition, comprising trabectedin and a first excipient, wherein the first excipient is one or more selected from the group consisting of monosaccharide and polyol. Preferably, the first excipient according to the present invention can be selected from the group consisting of monosaccharides, such as one or more of glucose, fructose, and galactose, and can also be selected from the group consisting of polyols, such as one or more of sorbitol, mannitol, glycerol, and lactitol. The first excipient can be preferably glucose, sorbitol or a mixture of both.

The main effect of the first excipient in the pharmaceutical composition of the present invention is to improve the stability of the active ingredient trabectedin in the lyophilization process.

In a preferred embodiment, the composition of the present invention also comprises a second excipient that mainly plays a protective role in storage process. The second excipient can be selected from the group consisting of polymer materials, such as one or more of albumin, dextran, hydroxyethyl starch, sodium carboxymethyl cellulose, hydroxypropyl beta cyclodextrin, maltodextrin, and polyethylene glycol.

The dextran used in the present invention is preferably dextran 40.

Any of the aforementioned first excipient and second excipient can be combined. A preferred combination comprises the first excipient selected from the group consisting of glucose, and the second excipient that is one or more selected from the group consisting of albumin, dextran, hydroxyethyl starch, sodium carboxymethyl cellulose, and hydroxypropyl beta cyclodextrin; or the first excipient selected from the group consisting of sorbitol, and the second excipient that is one or more selected from the group consisting of albumin, dextran, hydroxyethyl starch, sodium carboxymethyl cellulose, and hydroxypropyl beta cyclodextrin.

Although the first excipient used in the pharmaceutical composition of the present invention can improve the stability of trabectedin in the lyophilization process, the glass transition temperature of the first excipient is low, thereby resulting in a poor formability of the lyophilized product, and a slightly poor stability in the storage process. Therefore in a preferred embodiment, the first excipient is used in combination with the second excipient that has a higher glass transition temperature and a higher hygroscopicity, thereby further improving the appearance and storage stability of the lyophilized product.

The protective effect of the composition in the ET743 lyophilized formulation of the present invention is mainly reflected in the two processes—lyophilization and storage. 1) Lyophilization process: the hydroxyl groups in the protective agent can compete with the hydroxyl groups in water so as to play a protective role; 2) storage process: the amorphous material, especially the polymer material in the protective agent has a high hygroscopicity, therefore, it can keep a low relative humidity in a closed environment such as a vial, thereby playing a protective role.

In addition to the above excipients, the composition of the present invention also comprises a buffer. The buffer is selected from the group consisting of phosphate buffer, lactate buffer, acetate buffer, and citrate buffer, preferably one of potassium dihydrogen phosphate and sodium dihydrogen phosphate.

In the pharmaceutical composition of the present invention, the weight ratio of trabectedin to the first excipient is 1:10 to 1:2000, preferably 1:20 to 1:1500, more preferably 1:30 to 1:1000, and most preferably 1:40 to 1:500.

In the pharmaceutical composition of the present invention, the weight ratio of trabectedin to the second excipient is 1:10 to 1:1000, preferably 1:10 to 1:500, more preferably 1:10 to 1:300, and most preferably 1:10 to 1:100.

In a particularly preferred embodiment of the invention, the first excipient is glucose, and the second excipient is dextran. The weight ratio of glucose to dextran is 1:1 to 10:1, and preferably 1:1 to 1.5:1. In a more preferred embodiment, the weight of glucose accounts for 2-15%, and preferably 5-8% of the total weight of the composition, and the weight of dextran accounts for 1-10%, and preferably 3-5% of the total weight of the composition. In a most preferred embodiment, the weight of glucose and the weight of dextran account for 6.65% and 4.55% of the total weight of the composition, respectively.

Since a change in pH will affect the stability of trabectedin, a buffer is needed to maintain the pH of the system in a specific range. The weight ratio of trabectedin to the buffer is preferably 1:10 to 1:100, more preferably 1:15 to 1:50, and most preferably 1:20 to 1:40.

The composition of the present invention can be prepared into the form of a lyophilized formulation.

The above-mentioned ingredients are first formulated into a form of pre-lyophilization solution. The pH of the described pre-lyophilization solution can be 3-5, preferably 3.5-4.5, more preferably 3.6-4.2, and most preferably 3.9-4.1. If the pH value of the solution prepared only by the aforementioned ingredients is not within the desired range, the pH value can be adjusted by a pH regulator, for example, one or more pH regulators selected from the group consisting of phosphoric acid, acetic acid, tartaric acid, citric acid, citric acid, sodium hydroxide, and potassium hydroxide, preferably phosphoric acid and potassium hydroxide.

In the pre-lyophilization solution according to the present invention, the content of trabectedin is 0.1-0.5 mg/mL, preferably 0.2-0.3 mg/mL, and more preferably 0.25 mg/mL; the content of the protective agent is 10-100 mg/mL, preferably 20-80 mg/mL, and more preferably 20-60 mg/mL; the content of the excipient is 1-100 mg/mL, preferably 5-50 mg/mL, and more preferably 5-30 mg/mL; and the content of the buffer is 1-10 mg/mL, preferably 4-8 mg/mL, and more preferably 6-7 mg/mL.

The present invention also provides an injection of trabectedin that is obtained by reconstitution of the aforementioned lyophilized formulation.

The pharmaceutical composition of the present invention can be prepared by the following method:

1) dissolving trabectedin in an acidic buffer salt solution to obtain a buffer solution of trabectedin, wherein preferably the acid is phosphoric acid, and the buffer salt is potassium dihydrogen phosphate;

2) dissolving the desired first excipient and second excipient in a buffer salt solution, and adjusting the pH to a set value;

3) mixing well the above two solutions, and then adjusting the pH to a set value.

In order to obtain a lyophilized formulation, the method also comprises a step of lyophilizing the mixed solution of step 3).

The lyophilized formulation of the present invention can be prepared by a conventional lyophilization process in the art. For example, the lyophilization process of the present invention includes three stages of pre-freezing, primary drying, and secondary sublimation. The pre-freezing temperature is −25 to −50° C., the primary drying temperature is −10 to −40° C., and the secondary drying temperature is 15 to 30° C. During the primary drying and secondary drying, the vacuum degree is 0.1-0.5 mbar. Nitrogen gas is charged before the end of the lyophilizing process, and preferably 5-10 minutes before the end of the lyophilizing process.

The pharmaceutical composition provided by the present invention has a high stability, and is easy for industrial production.

DETAILED DESCRIPTION OF THE INVENTION

EXAMPLE 1

Figure 1A:
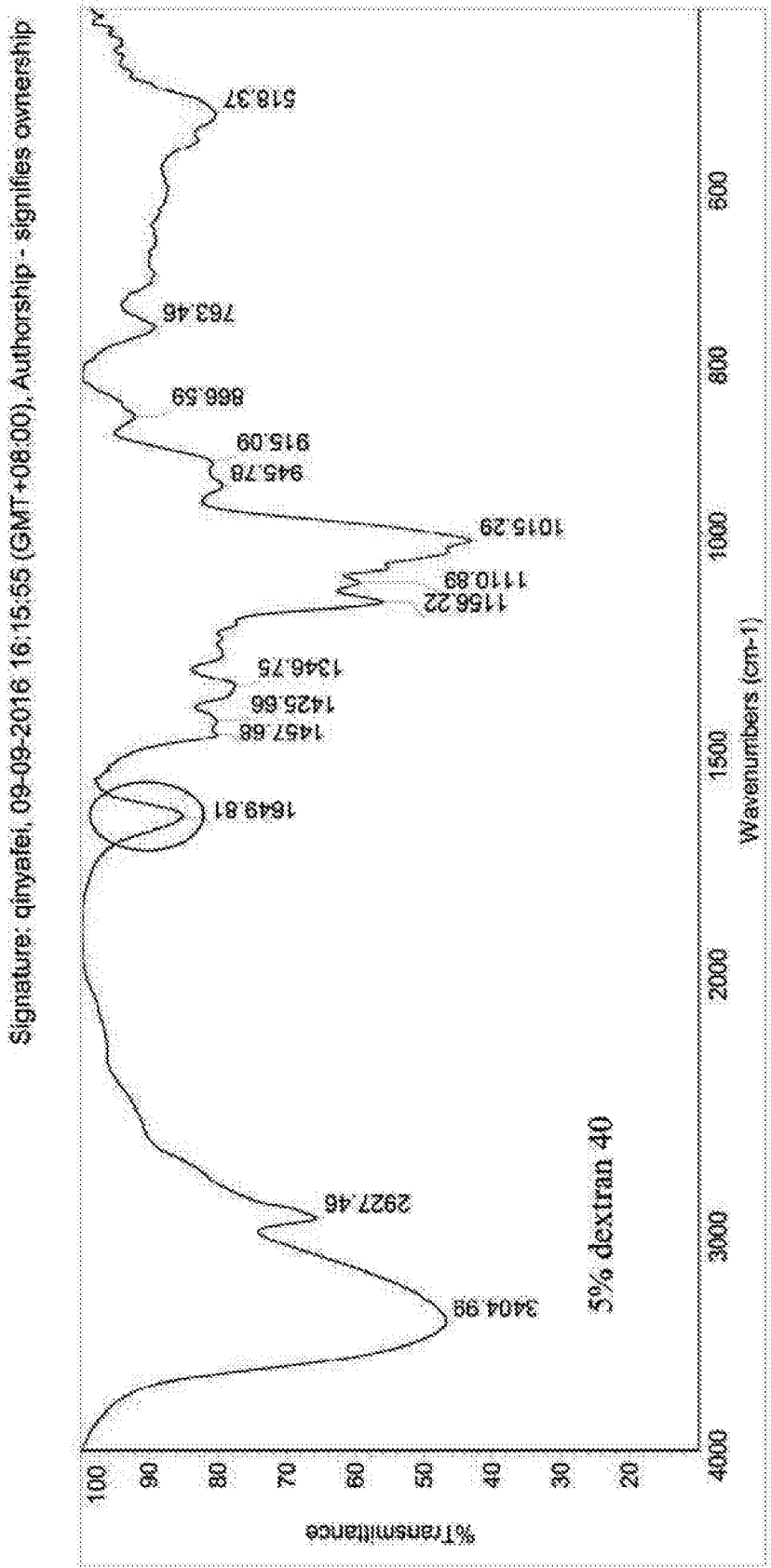
FIG. 1A: The infrared scanning spectrum of lyophilized sample (5% dextran 40, the water content of dextran 40 is 9%, and the actual dosage of dextran 40 is 4.55%).

The pre-lyophilization solution of trabectedin was prepared using trabectedin as the active ingredient, glucose as the first excipient, hydroxyethyl starch as the second excipient, potassium dihydrogen phosphate as the buffer, phosphoric acid/potassium hydroxide as the pH regulator, and water for injection as the solvent. The specific ingredients of the formulation and their dosages are as follows:

| Ingredients | Effect | Lot Size | 15 mL |
|---|---|---|---|
| Trabectedin | Active ingredient | 0.25 mg/mL | 3.75 mg |
| Phosphoric acid, 0.1N | Solvent/pH regulator | 0.043 mg/mL | 0.645 mL |
| Glucose | First excipient | 50 mg/mL | 750 mg |
| Hydroxyethyl starch | Second excipient | 30 mg/mL | 450 mg |
| Potassium dihydrogen phosphate | pH regulator | 6.8 mg/mL | 102 mg |
| Phosphoric acid, 1N/ potassium hydroxide, 0.1M | pH regulator | pH 3.6-4.2 | q.s. |
| Water for injection | Solvent | | q.s. to the total weight |

Preparation Method:
1. 102 mg of potassium dihydrogen phosphate was added to 2 mL of water, then 0.645 mL of phosphoric acid (0.1 N) was added, and the mixture was stirred well to obtain a potassium dihydrogen phosphate/phosphoric acid buffer solution;
2. 3.75 mg of trabectedin was added to the above potassium dihydrogen phosphate/phosphoric acid buffer solution, and the mixture was stirred until the drug was completely dissolved to obtain a drug solution;
3. 750 mg of glucose and 450 mg of hydroxyethyl starch were added to 9 mL of water for injection, and the mixture was dissolved with stirring, and then the pH was adjusted to 3.9±0.3 with a certain concentration of phosphoric acid solution;
4. the drug solution of step 2 was added to the solution of step 3 and mixed well, and then the pH of the resulting solution was adjusted to 3.9±0.3 with a certain concentration of phosphoric acid solution or potassium hydroxide solution;
5. the above solution was set to the total weight, and filled into a container that was then partially stoppered.

The above intermediate solution was lyophilized to prepare a lyophilized trabectedin formulation. The appearance, water content, reconstitution and pH were investigated. The change of related substances after lyophilization and the placement stability under accelerated conditions (25° C. 60% RH) and long-term conditions (2-8° C.) were measured.

TABLE 1

Appearance, water content, reconstitution and pH of the lyophilized product

| Appearance | Water content | Reconstitution | pH | Reconstituted solution |
|---|---|---|---|---|
| White cake | 1.6643% | Good | 3.92 | Clear solution |

TABLE 2

Measurement of related substances and placement stability

| Items | ET-701 (%) | ET-745 (%) | ET-759B (%) | ET-789A (%) | Total impurities (%) |
|---|---|---|---|---|---|
| Lyophilized formulation | 0.07 | 0.54 | / | / | 1.75 |
| Accelerated 1M | 0.10 | 0.53 | / | / | 1.76 |
| Accelerated 2M | 0.16 | 0.54 | / | / | 1.79 |
| Accelerated 3M | 0.42 | 0.57 | / | / | 2.09 |
| Accelerated 6M | 0.91 | 0.51 | 0.11 | / | 3.13 |
| Long-term 3M | 0.06 | 0.56 | / | / | 1.70 |
| Long-term 6M | 0.10 | 0.50 | 0.11 | / | 2.10 |

Experimental conclusions and analysis: The lyophilized product was prepared using glucose as the first excipient and hydroxyethyl starch as the second excipient. The appearance, water content and pH of the lyophilized product meet the requirement, and the reconstitution is good. The lyophilized formulation has a good stability under long-term conditions and accelerated conditions. It is demonstrated that the composition of glucose and hydroxyethyl starch can be used as a lyoprotectant of the trabectedin formulation to improve the stability of trabectedin in the lyophilization process and the storage process.

EXAMPLE 2

The pre-lyophilization solution of trabectedin was prepared using trabectedin as the active ingredient, glucose as the first excipient, sodium carboxymethyl cellulose as the second excipient, potassium dihydrogen phosphate as the buffer, phosphoric acid/potassium hydroxide as the pH regulator, and water for injection as the solvent.

The specific ingredients of the formulation and their dosages are as follows:

| Ingredients | Effect | Lot Size | 15 mL |
|---|---|---|---|
| Trabectedin | Active ingredient | 0.25 mg/mL | 3.75 mg |
| Phosphoric acid, 0.1N | Solvent/pH regulator | 0.043 mg/mL | 0.645 mL |

-continued

| Ingredients | Effect | Lot Size | 15 mL |
|---|---|---|---|
| Glucose | First excipient | 87.5 mg/mL | 1.3125 g |
| Sodium carboxymethyl cellulose | Second excipient | 37.5 mg/mL | 562.5 mg |
| Potassium dihydrogen phosphate | pH regulator | 6.8 mg/mL | 102 mg |
| Phosphoric acid, 1N/ potassium hydroxide, 0.1M | pH regulator | pH 3.6-4.2 | q.s. |
| Water for injection | Solvent | q.s. to the total weight | |

Preparation Method:

1. 102 mg of potassium dihydrogen phosphate was added to 2 mL of water, then 0.645 mL of phosphoric acid (0.1 N) was added, and the mixture was stirred well to obtain a potassium dihydrogen phosphate/phosphoric acid buffer solution;

2. 3.75 mg of trabectedin was added to the above potassium dihydrogen phosphate/phosphoric acid buffer solution, and the mixture was stirred until the drug was completely dissolved to obtain a drug solution;

3. 1.3125 g of glucose and 562.5 mg of sodium carboxymethyl cellulose were added to 9 mL of water for injection, and the mixture was dissolved with stirring, and then the pH was adjusted to 3.9±0.3 with a certain concentration of phosphoric acid solution;

4. the drug solution of step 2 was added to the solution of step 3 and mixed well, and then the pH of the resulting solution was adjusted to 3.9±0.3 with a certain concentration of phosphoric acid solution or potassium hydroxide solution;

5. the above solution was set to the total weight, and filled into a container that was then partially stoppered.

The above intermediate solution was lyophilized to prepare a lyophilized trabectedin formulation. The appearance, water content, reconstitution and pH were investigated. The change of related substances after lyophilization and the placement stability under accelerated conditions (25° C. 60% RH) and long-term conditions (2-8° C.) were measured.

TABLE 3

Appearance, water content, reconstitution and pH of the lyophilized product

| Appearance | Water content | Reconstitution | pH | Reconstituted solution |
|---|---|---|---|---|
| White cake | 5.8619% | Good | 3.92 | Clear solution |

TABLE 4

Measurement of related substances and placement stability

| Items | ET-701 (%) | ET-745 (%) | ET-759B (%) | ET-789A (%) | Total impurities (%) |
|---|---|---|---|---|---|
| Lyophilized formulation | 0.06 | 0.52 | / | / | 1.72 |
| Accelerated 25° C. 3M | 0.21 | 0.55 | / | / | 1.61 |
| Long-term 2-8° C. 3M | 0.05 | 0.53 | / | / | 1.32 |

Experimental conclusions and analysis: The lyophilized product was prepared using glucose as the first excipient and sodium carboxymethyl cellulose as the second excipient. The appearance, water content and pH of the lyophilized product meet the requirement, and the reconstitution is good. The lyophilized formulation has a good stability under long-term conditions and accelerated conditions. It is demonstrated that the composition of glucose and sodium carboxymethyl cellulose can be used as a lyoprotectant of the trabectedin formulation to improve the stability of trabectedin in the lyophilization process and the storage process.

EXAMPLE 3

The pre-lyophilization solution of trabectedin was prepared using trabectedin as the active ingredient, glucose as the first excipient, dextran 40 as the second excipient, potassium dihydrogen phosphate as the buffer, phosphoric acid/potassium hydroxide as the pH regulator, and water for injection as the solvent. The specific ingredients of the formulation and their dosages are as follows:

| Ingredients | Effect | Lot Size | 15 mL |
|---|---|---|---|
| Trabectedin | Active ingredient | 0.25 mg/mL | 3.75 mg |
| Phosphoric acid, 0.1N | Solvent/pH regulator | 0.043 mg/mL | 0.645 mL |
| Glucose | First excipient | 50 mg/mL | 750 mg |
| Dextran 40 | Second excipient | 30 mg/mL | 450 mg |
| Potassium dihydrogen phosphate | pH regulator | 6.8 mg/mL | 102 mg |
| Phosphoric acid, 1N/ potassium hydroxide, 0.1M | pH regulator | pH 3.6-4.2 | q.s. |
| Water for injection | Solvent | q.s. to the total weight | |

Preparation Method:

1. 102 mg of potassium dihydrogen phosphate was added to 2 mL of water, then 0.645 mL of phosphoric acid (0.1 N) was added, and the mixture was stirred well to obtain a potassium dihydrogen phosphate/phosphoric acid buffer solution;

2. 3.75 mg of trabectedin was added to the above potassium dihydrogen phosphate/phosphoric acid buffer solution, and the mixture was stirred until the drug was completely dissolved to obtain a drug solution;

3. 750 mg of glucose and 450 mg of dextran 40 were added to 9 mL of water for injection, and the mixture was dissolved with stirring, and then the pH was adjusted to 3.9±0.3 with a certain concentration of phosphoric acid solution;

4. the drug solution of step 2 was added to the solution of step 3 and mixed well, and then the pH of the resulting solution was adjusted to 3.9±0.3 with a certain concentration of phosphoric acid solution or potassium hydroxide solution;

5. the above solution was set to the total weight, and filled into a container that was then partially stoppered.

The above intermediate solution was lyophilized to prepare a lyophilized trabectedin formulation. The appearance, water content, reconstitution and pH were investigated. The change of related substances after lyophilization and the placement stability under accelerated conditions (25° C. 60% RH) and long-term conditions (2-8° C.) were measured.

TABLE 5

Appearance, water content, reconstitution and pH of the lyophilized product

| Appearance | Water content | Reconstitution | pH | Reconstituted solution |
|---|---|---|---|---|
| White cake | 2.6829% | Good | 3.91 | Clear solution |

TABLE 6

Measurement of related substances and placement stability

| Items | ET-701 (%) | ET-745 (%) | ET-759B (%) | ET-789A (%) | Total impurities (%) |
|---|---|---|---|---|---|
| Lyophilized formulation | 0.08 | 0.54 | / | / | 1.72 |
| Accelerated 1M | 0.08 | 0.53 | / | / | 1.70 |
| Accelerated 2M | 0.16 | 0.54 | / | / | 1.78 |
| Accelerated 3M | 0.21 | 0.56 | / | / | 1.81 |
| Accelerated 6M | 0.59 | 0.51 | 0.11 | / | 2.64 |
| Long-term 3M | 0.05 | 0.58 | / | / | 1.67 |
| Long-term 6M | 0.11 | 0.51 | 0.10 | / | 1.93 |

Experimental conclusions and analysis: The lyophilized product was prepared using glucose as the first excipient and dextran 40 as the second excipient. The appearance, water content and pH of the lyophilized product meet the requirement, and the reconstitution is good. The lyophilized formulation has a good stability under long-term conditions and accelerated conditions. It is demonstrated that the composition of glucose and dextran 40 can be used as a lyoprotectant of the trabectedin formulation to improve the stability of trabectedin in the lyophilization process and the storage process.

EXAMPLE 4

The pre-lyophilization solution of trabectedin was prepared using trabectedin as the active ingredient, glucose as the first excipient, hydroxypropyl beta cyclodextrin as the second excipient, potassium dihydrogen phosphate as the buffer, phosphoric acid/potassium hydroxide as the pH regulator, and water for injection as the solvent. The specific ingredients of the formulation and their dosages are as follows:

| Ingredients | Effect | Lot Size | 15 mL |
|---|---|---|---|
| Trabectedin | Active ingredient | 0.25 mg/mL | 3.75 mg |
| Phosphoric acid, 0.1N | Solvent/pH regulator | 0.043 mg/mL | 0.645 mL |
| Glucose | First excipient | 50 mg/mL | 750 mg |
| Hydroxypropyl beta cyclodextrin | Second excipient | 50 mg/mL | 750 mg |
| Potassium dihydrogen phosphate | pH regulator | 6.8 mg/mL | 102 mg |
| Phosphoric acid, 1N/ potassium hydroxide, 0.1M | pH regulator | pH 3.6-4.2 | q.s. |
| Water for injection | Solvent | | q.s. to the total weight |

Preparation Method:
1. 102 mg of potassium dihydrogen phosphate was added to 2 mL of water, then 0.645 mL of phosphoric acid (0.1 N) was added, and the mixture was stirred well to obtain a potassium dihydrogen phosphate/phosphoric acid buffer solution;
2. 3.75 mg of trabectedin was added to the above potassium dihydrogen phosphate/phosphoric acid buffer solution, and the mixture was stirred until the drug was completely dissolved to obtain a drug solution;
3. 750 mg of glucose and 750 mg of hydroxypropyl beta cyclodextrin were added to 9 mL of water for injection, and the mixture was dissolved with stirring, and then the pH was adjusted to 3.9±0.3 with a certain concentration of phosphoric acid solution;
4. the drug solution of step 2 was added to the solution of step 3 and mixed well, and then the pH of the resulting solution was adjusted to 3.9±0.3 with a certain concentration of phosphoric acid solution or potassium hydroxide solution;
5. the above solution was set to the total weight, and filled into a container that was then partially stoppered.

The above intermediate solution was lyophilized to prepare a lyophilized trabectedin formulation. The appearance, water content, reconstitution and pH were investigated. The change of related substances after lyophilization and the placement stability under accelerated conditions (25° C. 60% RH) and long-term conditions (2-8° C.) were measured.

TABLE 7

Appearance, water content, reconstitution and pH of the lyophilized product

| Appearance | Water content | Reconstitution | pH | Reconstituted solution |
|---|---|---|---|---|
| White cake | 1.3506% | Good | 3.94 | Clear solution |

TABLE 8

Measurement of related substances and placement stability

| Items | ET-701 (%) | ET-745 (%) | ET-759B (%) | ET-789A (%) | Total impurities (%) |
|---|---|---|---|---|---|
| Lyophilized formulation | 0.07 | 0.63 | / | / | 1.94 |
| Accelerated 1M | 0.06 | 0.59 | / | / | 1.86 |
| Accelerated 2M | 0.11 | 0.63 | / | / | 1.98 |
| Accelerated 3M | 0.12 | 0.55 | / | / | 1.80 |
| Long-term 1M | 0.05 | 0.58 | / | / | 1.80 |
| Long-term 3M | 0.05 | 0.51 | / | / | 1.69 |

Experimental conclusions and analysis: The lyophilized product was prepared using glucose as the first excipient and hydroxypropyl beta cyclodextrin as the second excipient. The appearance, water content and pH of the lyophilized product meet the requirement, and the reconstitution is good. The lyophilized formulation has a good stability under long-term conditions and accelerated conditions. It is demonstrated that the composition of glucose and dextran 40 can be used as a lyoprotectant of the trabectedin formulation to improve the stability of trabectedin in the lyophilization process and the storage process.

EXAMPLE 5

The pre-lyophilization solution of trabectedin was prepared using trabectedin as the active ingredient, sorbitol as the first excipient, sodium carboxymethyl cellulose as the second excipient, potassium dihydrogen phosphate as the buffer, phosphoric acid/potassium hydroxide as the pH regulator, and water for injection as the solvent.

The specific ingredients of the formulation and their dosages are as follows:

| Ingredients | Effect | Lot Size | 15 mL |
|---|---|---|---|
| Trabectedin | Active ingredient | 0.25 mg/mL | 3.75 mg |
| Phosphoric acid, 0.1N | Solvent/pH regulator | 0.043 mg/mL | 0.645 mL |
| Sorbitol | First excipient | 100 mg/mL | 1.5 g |
| Sodium carboxymethyl cellulose | Second excipient | 25 mg/mL | 375 mg |
| Potassium dihydrogen phosphate | pH regulator | 6.8 mg/mL | 102 mg |
| Phosphoric acid, 1N/ potassium hydroxide, 0.1M | pH regulator | pH 3.6-4.2 | q.s. |
| Water for injection | Solvent | q.s. to the total weight | |

Preparation Method:

1. 102 mg of potassium dihydrogen phosphate was added to 2 mL of water, then 0.645 mL of phosphoric acid (0.1 N) was added, and the mixture was stirred well to obtain a potassium dihydrogen phosphate/phosphoric acid buffer solution;

2. 3.75 mg of trabectedin was added to the above potassium dihydrogen phosphate/phosphoric acid buffer solution, and the mixture was stirred until the drug was completely dissolved to obtain a drug solution;

3. 1.5 g of sorbitol and 375 mg of sodium carboxymethyl cellulose were added to 9 mL of water for injection, and the mixture was dissolved with stirring, and then the pH was adjusted to 3.9±0.3 with a certain concentration of phosphoric acid solution;

4. the drug solution of step 2 was added to the solution of step 3 and mixed well, and then the pH of the resulting solution was adjusted to 3.9±0.3 with a certain concentration of phosphoric acid solution or potassium hydroxide solution;

5. the above solution was set to the total weight, filled into a container that was then partially stoppered, and lyophilized.

The above intermediate solution was lyophilized to prepare a lyophilized trabectedin formulation. The appearance, water content, reconstitution and pH were investigated. The change of related substances after lyophilization and the placement stability under accelerated conditions (25° C. 60% RH) and long-term conditions (2-8° C.) were measured.

TABLE 9

Appearance, water content, reconstitution and pH of the lyophilized product

| Appearance | Water content | Reconstitution | pH | Reconstituted solution |
|---|---|---|---|---|
| White cake | 8.0654% | Good | 3.91 | Clear solution |

TABLE 10

Measurement of related substances and placement stability

| Items | ET-701 (%) | ET-745 (%) | ET-759B (%) | ET-789A (%) | Total impurities (%) |
|---|---|---|---|---|---|
| Lyophilized formulation | 0.10 | 0.48 | / | / | 1.52 |
| Accelerated 25° C. 3M | 0.70 | 0.57 | 0.27 | / | 2.65 |
| Long-term 2-8° C. 3M | 0.17 | 0.55 | 0.10 | / | 1.60 |

Experimental conclusions and analysis: The lyophilized product was prepared using sorbitol as the first excipient and sodium carboxymethyl cellulose as the second excipient. The appearance, water content and pH of the lyophilized product meet the requirement, and the reconstitution is good. The lyophilized formulation has a good stability under long-term conditions and accelerated conditions. It is demonstrated that the composition of sorbitol and sodium carboxymethyl cellulose can be used as a lyoprotectant of the trabectedin formulation to improve the stability of trabectedin in the lyophilization process and the storage process.

EXAMPLE 6

In order to optimize the proportion and dosage of dextran 40/glucose, we have used the Response Surface Methodology-Central Composite Design (RSM-CCD), wherein the dosage of dextran 40 is limited to 2%-5%, and the dosage of glucose is limited to 4%-10%. Design Expert software designed a total of 13 formulations. The test results of related substance of the lyophilized product at the initial point and accelerated 2M are shown in Table 11 below:

TABLE 11

Effect of different ratios of glucose/dextran 40 on product stability

| Glucose:dextran 40 (w:w) | Time | ET-701 (%) | ET-745 (%) | ET-759B (%) | ET-789A (%) | ETHO2 (%) | Total impurities (%) |
|---|---|---|---|---|---|---|---|
| 2.76:3.50 | Initial point | 0.07 | 0.73 | / | / | / | 2.14 |
|  | Accelerated 2M | 0.14 | 0.72 | / | / | / | 2.45 |
| 10:2 | Initial point | 0.12 | 0.54 | / | / | / | 1.62 |
|  | Accelerated 2M | 0.88 | 0.55 | / | / | / | 2.48 |
| 7:3.5 | Initial point | 0.07 | 0.53 | / | / | / | 1.74 |
|  | Accelerated 2M | 0.15 | 0.54 | / | / | / | 1.78 |
| 7:1.38 | Initial point | 0.11 | 0.54 | / | / | / | 1.66 |
|  | Accelerated 2M | 0.99 | 0.55 | / | / | / | 2.86 |
| 4:5 | Initial point | 0.07 | 0.62 | / | / | / | 1.95 |
|  | Accelerated 2M | 0.11 | 0.63 | / | / | / | 2.17 |
| 10:5 | Initial point | 0.08 | 0.55 | / | / | / | 1.62 |
|  | Accelerated 2M | 0.15 | 0.54 | / | / | / | 1.80 |

TABLE 11-continued

Effect of different ratios of glucose/dextran 40 on product stability

| Glucose:dextran 40 (w:w) | Time | ET-701 (%) | ET-745 (%) | ET-759B (%) | ET-789A (%) | ETHO2 (%) | Total impurities (%) |
|---|---|---|---|---|---|---|---|
| 4:2 | Initial point | 0.08 | 0.54 | / | / | / | 1.63 |
|  | Accelerated 2M | 0.20 | 0.54 | / | / | / | 1.87 |
| 11.24:3.5 | Initial point | 0.10 | 0.55 | / | / | / | 1.59 |
|  | Accelerated 2M | 0.44 | 0.55 | / | / | / | 2.11 |
| 7:5.62 | Initial point | 0.07 | 0.55 | / | / | / | 1.69 |
|  | Accelerated 2M | 0.07 | 0.56 | / | / | / | 1.80 |

In addition, the appearance of lyophilized products was also investigated, as shown in Table 12:

TABLE 12

Appearance of lyophilized products comprising different ratios of glucose/dextran 40

| Glucose:dextran 40 (w:w) | Appearance |
|---|---|
| 2.76:3.50 | Good |
| 10:2 | Severe shrinkage |
| 7:3.5 | Bottom shrinkage |
| 7:1.38 | Severe shrinkage |
| 4:5 | Good |
| 10:5 | Bottom shrinkage |
| 4:2 | Bottom severe shrinkage |
| 11.24:3.5 | Severe shrinkage |
| 7:5.62 | Good |

Results and Analysis:

The Design Expert software was used to analyze and predict the optimal dosage of glucose/dextran 40 using the total impurities at the initial point and accelerated 2M, ET-701 at the initial point and accelerated 2M, and the appearance as response values.

The simulation result shows that when the dosage of dextran 40 is 5% (water content is 9%) and the dosage of glucose is 6.65%, the total impurities and ET-701 at the initial point are 1.800% and 0.066% respectively, the total impurities and ET-701 at accelerated 2M are 1.799% and 0.059% respectively, and the appearance score is 2.707 (the best appearance score is 3), which meet the our requirement for formulation. Therefore, the optimal dosages of glucose and dextran 40 (absolute dosages) are 6.65% and 4.55% respectively.

EXAMPLE 7

In order to demonstrate the effect of dextran 40 in the lyophilization and long-term storage process, in-depth study was carried out by means of infrared spectroscopy and differential scanning calorimetry (DSC).

(1) Infrared Characterization of Intermolecular Hydrogen Bonds

Figure 1B:
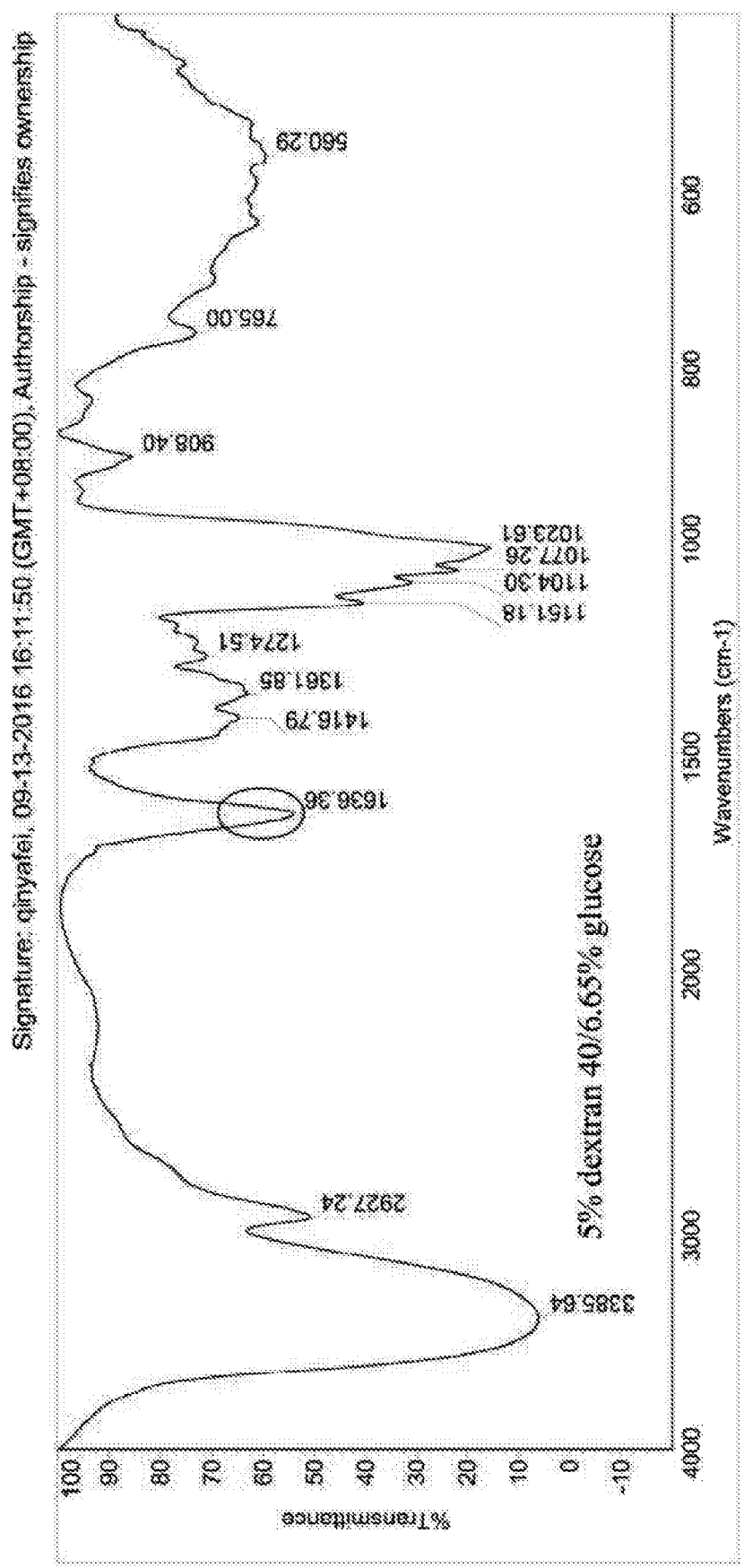
FIG. 1B: The infrared scanning spectrum of lyophilized sample (5% dextran 40/6.65% glucose, the water content of dextran 40 is 9%, and the actual dosage of dextran 40 is 4.55%).

Infrared scans were performed on lyophilized samples comprising only 4.55% of dextran 40 and simultaneously comprising 4.55% of dextran 40 and 6.65% of glucose. The results (FIG. 1A and FIG. 1B) show that, in the lyophilized sample comprising 4.55% of dextran 40, the stretching vibration peak of the aldehyde group in dextran 40 appears at wave number of 1649.81. However, in the sample comprising 4.55% of dextran 40 and 6.65% of glucose, this peak appears at wave number of 1636.36. It is demonstrated that there is a hydrogen bond interaction between the hydroxyl group in glucose and the aldehyde group in dextran 40, thereby resulting in a decrease in the stretching vibration amplitude of aldehyde group and a decrease in the wave number. (Note: The interaction between glucose and dextran 40 is mainly hydrogen bond interaction between hydroxyl groups. Due to the difficulty in characterizing hydrogen bond interaction, the characteristic peak of aldehyde group is chosen for characterization, because there is also a hydrogen bond interaction between aldehyde group and hydroxyl group.)

(2) Thermal Analysis of Lyophilized Samples by DSC

Figure 2A:
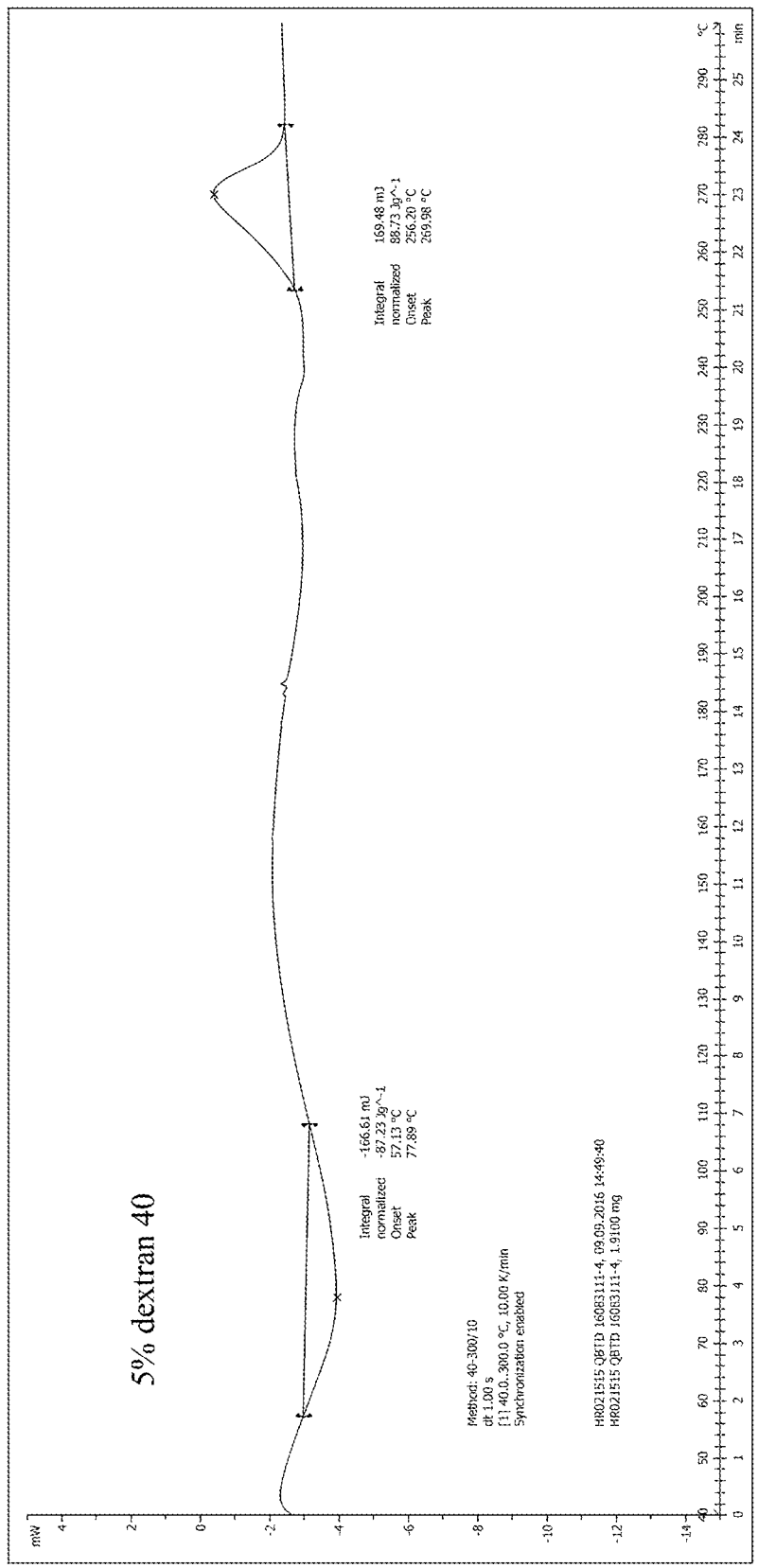
FIG. 2A: The differential scanning calorimetry (DSC) spectrum of lyophilized sample (5% dextran 40, the water content of dextran 40 is 9%, and the actual dosage of dextran 40 is 4.55%).
Figure 2B:
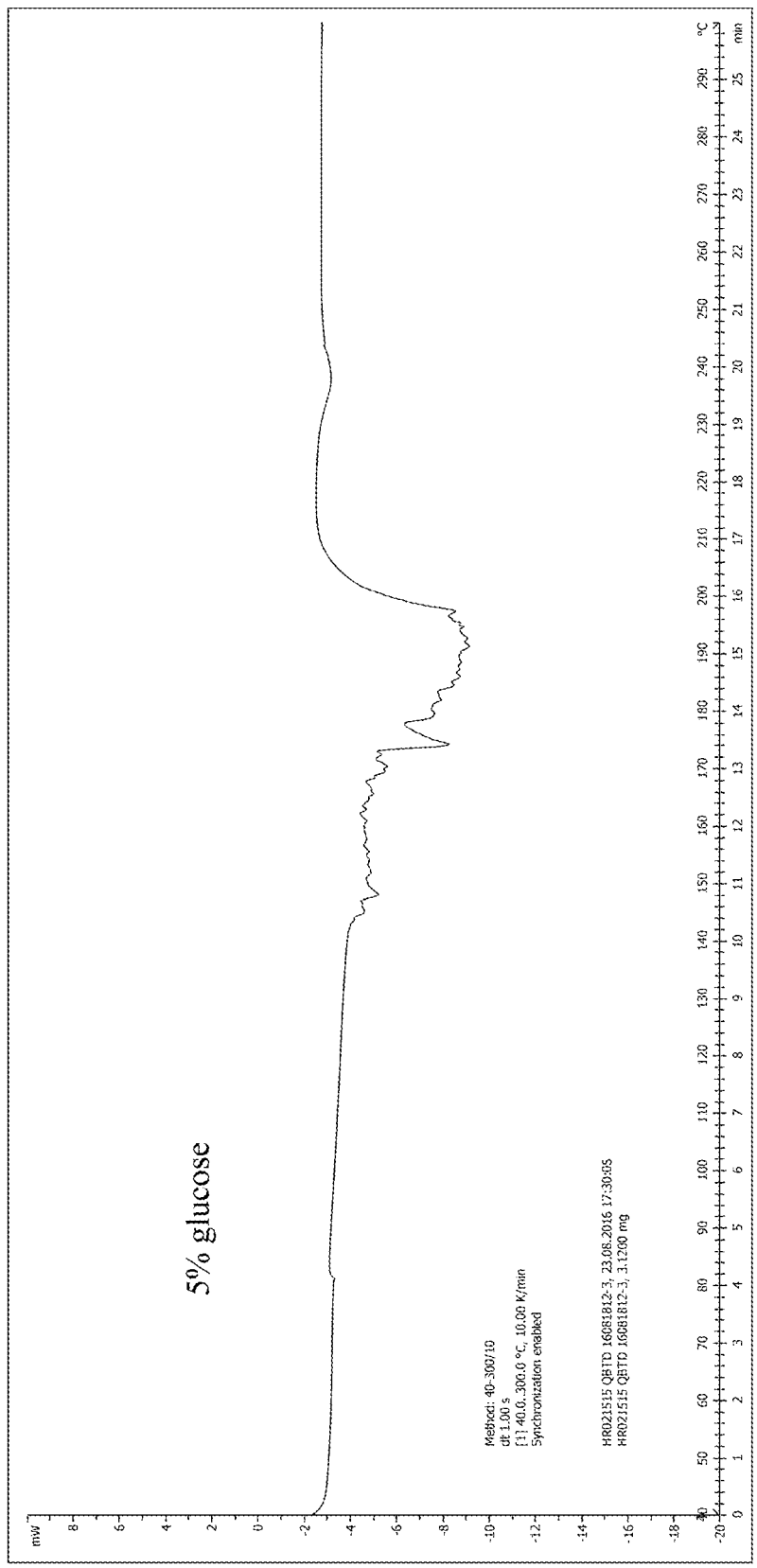
FIG. 2B: The DSC spectrum of lyophilized sample (5% glucose).
Figure 2C:
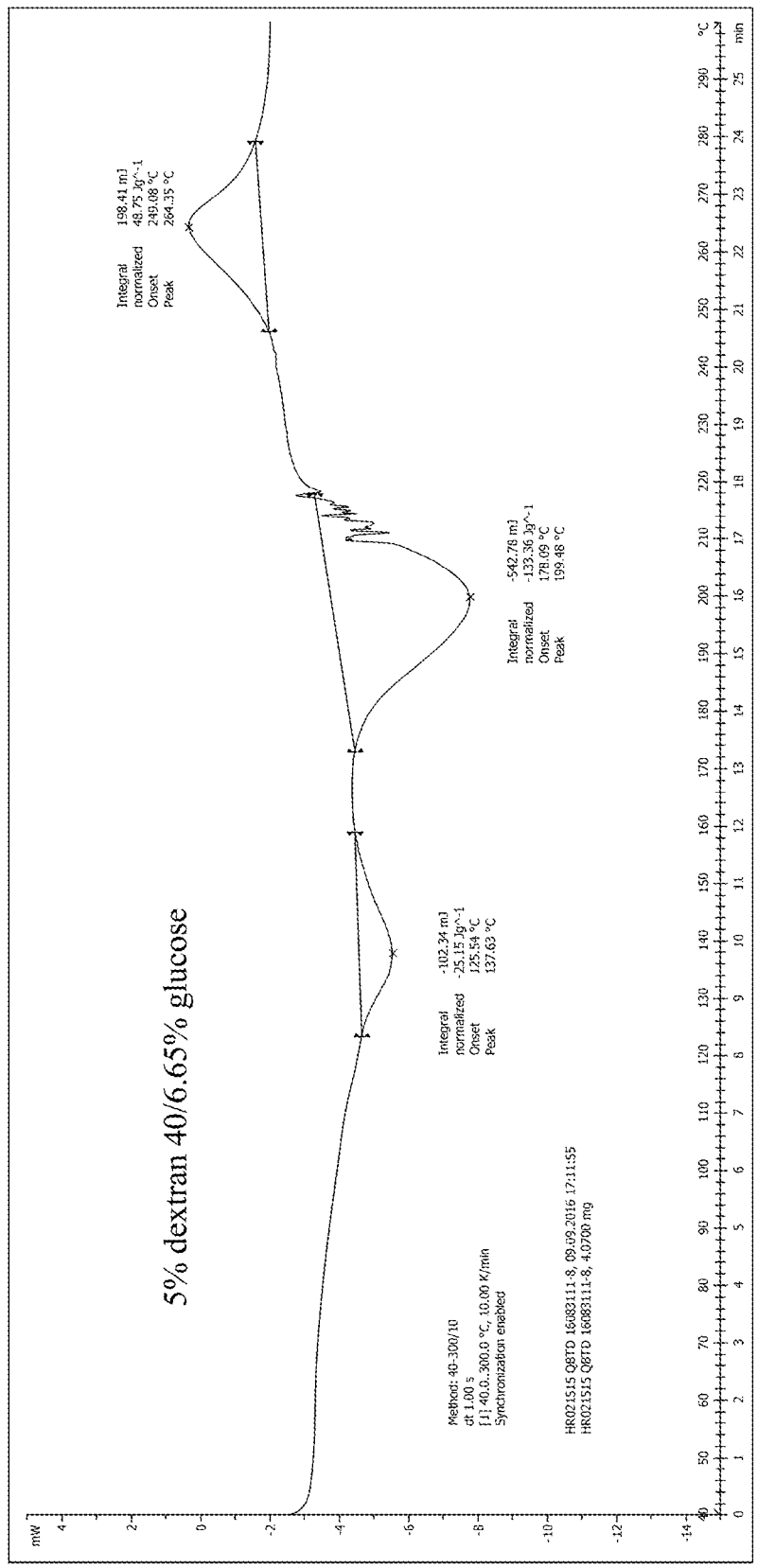
FIG. 2C: The DSC spectrum of lyophilized sample (5% dextran 40/6.65% glucose, the water content of dextran 40 is 9%, and the actual dosage of dextran 40 is 4.55%).

Due to the interaction between dextran 40 and glucose, DSC is also used to analyze the thermal response behavior of lyophilized samples. The results (FIG. 2A, FIG. 2B and FIG. 2C) show that, there are one endothermic peak and one exothermic peak in the DSC spectrum of the lyophilized sample comprising 4.55% of dextran 40; there is one wide endothermic peak in the lyophilized sample comprising 5% of glucose; while there are two endothermic peaks and one exothermic peak in the lyophilized sample comprising 4.55% of dextran 40 and 6.65% of glucose, and, due to the presence of glucose, the original endothermic peak of dextran 40 shifts toward the direction of high temperature, which further demonstrates the interaction between the two.

EXAMPLE 8

In order to further study the effect of the ratio of dextran 40/glucose on related substances, a high temperature test is designed to evaluate and validate the rationality and effectiveness of the optimal formulation. The test results are shown in Table 13.

TABLE 13

High-temperature stability of lyophilized products comprising different ratios of glucose/dextran 40

| Glucose:dextran 40 (w:w) | Time | ET-701 (%) | ET-745 (%) | ET-759B (%) | ET-789A (%) | ETHO2 (%) | Total impurities (%) |
|---|---|---|---|---|---|---|---|
| API | | / | 0.25 | 0.31 | / | / | 2.56 |
| 5:4.55 | Initial point | / | 0.26 | 0.24 | / | / | 2.39 |
| | 40° C. 10 d | / | 0.31 | 0.31 | / | / | 3.03 |
| | 60° C. 10 d | 3.43 | 1.09 | 0.43 | / | / | 32.82 |
| 5.5:4.55 | Initial point | / | 0.25 | 0.28 | / | / | 2.39 |
| | 40° C. 10 d | / | 0.27 | 0.31 | / | / | 2.89 |
| | 60° C. 10 d | 2.05 | 0.67 | 0.26 | / | / | 58.40 |
| 6:4.55 | Initial point | 0.04 | 0.23 | 0.24 | / | / | 2.38 |
| | 40° C. 10 d | / | 0.27 | 0.31 | / | / | 2.89 |
| | 60° C. 10 d | 3.82 | 1.13 | 0.50 | / | / | 33.30 |
| 6.65:4.55 (DoE formulation) | Initial point | / | 0.24 | 0.23 | / | / | 2.30 |
| | 40° C. 10 d | / | 0.26 | 0.30 | / | / | 2.88 |
| | 60° C. 10 d | 3.38 | 1.09 | 0.44 | / | / | 29.77 |
| 7:4.55 | Initial point | / | 0.23 | 0.26 | / | / | 2.35 |
| | 40° C. 10 d | / | 0.24 | 0.30 | / | / | 2.93 |
| | 60° C. 10 d | 3.59 | 1.17 | 0.43 | / | / | 30.84 |
| 7.5:4.55 | Initial point | 0.03 | 0.22 | 0.25 | / | / | 2.33 |
| | 40° C. 10 d | / | 0.26 | 0.28 | / | / | 2.85 |
| | 60° C. 10 d | 3.66 | 1.21 | 0.42 | / | / | 31.59 |
| 6.5:4.5 | Initial point | 0.03 | 0.23 | 0.25 | / | / | 2.39 |
| | 40° C. 10 d | / | 0.25 | 0.30 | / | / | 2.89 |
| | 60° C. 10 d | 3.87 | 1.23 | 0.46 | / | / | 33.54 |

Results and Analysis:

(1) Starting sample: The effect of different ratios of glucose to dextran 40 on related substances is mainly reflected in the total impurities. When ET-701 is at a low level, there are no significant differences in other known impurities. When the glucose and dextran 40 are higher or lower, a certain increase in the total impurities appears (Note: The difference is small).

(2) 40° C. 10 days

After 10 days at high temperature of 40° C., no significant change in the appearance of the sample was observed. The test results of related substances show that, after 10 days at 40° C., ET-701 increases significantly, and the unknown individual impurities increase, thereby resulting in an increase in total impurities. The increase degrees of different ratios of auxiliary materials are slightly different. Glucose:dextran 40=6.65%:4.55% is the optimal formulation.

(3) 60° C. 10 days

After 10 days at high temperature of 60° C., all samples showed severe shrinkage, and the sample comprising API appeared bright yellow. The test results of related substances show that, the total impurities increases significantly. With respect to formulations comprising different ratios of glucose/dextran 40, the degrees of increase of the total impurities are different. Glucose:dextran 40=6.65%:4.55% is the optimal formulation with the smallestincrease in the total impurities.

EXAMPLE 9

In order to meet the requirement of clinical use, the stability of the solution that was obtained by reconstituting the lyophilized product was investigated. 0.25 mg of a specification sample (the protective agents were 6.65% of glucose and 4.55% of dextran 40) was reconstituted in 5 mL of water for injection. The change of related substances at room temperature and refrigeration (2-8° C.) were investigated. The results are shown in Table 14 and Table 15 below:

TABLE 14

Stability of the solution of the product at room temperature

| Time | ET-701 (%) | ET-745 (%) | ET-759B (%) | ET-789A (%) | ETHO2 (%) | Main individual impurity (%) | Total impurities (%) |
|---|---|---|---|---|---|---|---|
| Initial point | 0.05 | 0.21 | 0.10 | / | / | 0.18 | 2.04 |
| 4 h | 0.05 | 0.21 | 0.13 | / | / | 0.19 | 2.22 |
| 8 h | 0.06 | 0.22 | 0.14 | / | / | 0.22 | 2.27 |
| 12 h | 0.07 | 0.22 | 0.17 | / | / | 0.22 | 2.35 |
| 24 h | 0.08 | 0.22 | 0.24 | / | / | 0.25 | 2.48 |

TABLE 15

Stability of the solution of the product under refrigeration (2-8° C.)

| Time | ET-701 (%) | ET-745 (%) | ET-759B (%) | ET-789A (%) | ETHO2 (%) | Main individual impurity (%) | Total impurities (%) |
|---|---|---|---|---|---|---|---|
| Initial point | 0.05 | 0.26 | 0.22 | / | / | 0.26 | 2.47 |
| 14 h | 0.05 | 0.25 | 0.23 | / | / | 0.26 | 2.51 |
| 37 h | 0.09 | 0.28 | 0.22 | / | / | 0.25 | 2.42 |

The results show that after reconstitution of the product, the impurities increase slowly at room temperature; after reconstitution of the product, the stability is good under refrigeration. Therefore, it is recommended that the sample should be used as soon as possible after reconstitution. The sample has to be refrigerated if it is intended to be stored for a period of time.

EXAMPLE 10

In order to further demonstrate the protective effect of glucose and dextran 40 6.65% and 4.55% respectively on the sample, the stability of the lyophilized sample under long-term conditions and accelerated conditions was investigated.

The pre-lyophilization solution of trabectedin was prepared using trabectedin as the active ingredient, glucose as the first excipient, dextran 40 as the second excipient, potassium dihydrogen phosphate as the buffer, phosphoric acid/potassium hydroxide as the pH regulator, and water for injection as the solvent. The specific ingredients of the formulation and their dosages are as follows:

| Ingredients | Effect | Lot Size | Dosage for 120 ml |
|---|---|---|---|
| Trabectedin | Active ingredient | 0.25 mg/mL | 30 mg |
| Phosphoric acid, 0.1N | Solvent/pH regulator | 0.043 g/ml | 5.16 ml |
| Potassium dihydrogen phosphate | Buffer | 6.8 mg/ml | 816 mg |
| Dextran 40 | Excipient | 49 mg/ml[1] | 5.88 g |
| Glucose | Excipient | 66.5 mg/ml | 7.98 g |
| Water for injection | Solvent | | q.s. to the total weight |

Note
[1]The water content of dextran 40 is 6.6%, and the actual concentration is 45.5 mg/mL.

Preparation Method:

1. At room temperature, 80 mL of water for injection was added to a 500 mL beaker, then 816 mg of potassium dihydrogen phosphate, 5.88 g of dextran 40 and 7.98 g of glucose were added, dissolved with stirring and mixed well.

2. 30 mg of trabectedin was added to 5.16 mL of phosphoric acid solution (0.1N), and dissolved with stirring.

3. The solution of step 2 was added to the solution of step 1 and mixed well, the pH was adjusted to 3.6 to 4.2 with phosphoric acid or potassium hydroxide, and the solution was set to the total weight.

4. The solution was filtered through a 0.22 μm membrane, and filled into 10 mL vials (specification: 0.25 mg, 1 mL/vial) or 20 mL vials (specification: 1 mg, 4 mL/vial).

5. The solution was lyophilized to prepare a lyophilized trabectedin formulation.

The above lyophilized formulations were stored under accelerated conditions (25° C. 60% RH), and the related substances and water content were measured at different time points.

TABLE 16

Measurement of related substances and stability under long-term conditions and accelerated conditions

| Specification | Items | ET-701 (%) | ET-745 (%) | ET-759B (%) | ET-789A (%) | Total impurities (%) |
|---|---|---|---|---|---|---|
| | API | / | 0.25 | 0.31 | / | 2.56 |
| 0.25 mg | Initial point | 0.05 | 0.23 | 0.20 | / | 2.51 |
| | Accelerated 25° C. 1M | 0.08 | 0.21 | 0.16 | / | 2.37 |
| | Accelerated 25° C. 2M | 0.09 | 0.26 | 0.28 | / | 2.56 |
| | Accelerated 25° C. 3M | 0.15 | 0.25 | 0.19 | / | 2.63 |
| | Long-term 2-8° C. 3M | 0.04 | 0.25 | 0.16 | / | 2.44 |
| 1 mg | Initial point | 0.05 | 0.22 | 0.22 | / | 2.46 |
| | Accelerated 25° C. 1M | 0.06 | 0.20 | 0.15 | / | 2.28 |
| | Accelerated 25° C. 2M | 0.05 | 0.21 | 0.12 | / | 2.36 |
| | Accelerated 25° C. 3M | 0.08 | 0.24 | 0.17 | / | 2.50 |
| | Long-term 2-8° C. 3M | 0.04 | 0.22 | 0.15 | / | 2.42 |

TABLE 17

Water content of the samples by TGA method

| Specification | Items | TGA (%) |
|---|---|---|
| 0.25 mg | Lyophilized formulation | 3.09 |
|  | Accelerated 25° C. 1M | 2.55 |
|  | Accelerated 25° C. 2M | 2.15 |
|  | Accelerated 25° C. 3M | 2.34 |
| 1 mg | Lyophilized formulation | 2.38 |
|  | Accelerated 25° C. 1M | 1.97 |
|  | Accelerated 25° C. 2M | 1.30 |
|  | Accelerated 25° C. 3M | 1.22 |

Results and analysis: The test results of related substances shows that, after being stored under accelerated conditions and long-term conditions for 3 months, there is no significant change in individual impurities and total impurities in the two specifications of the samples. Especially, under accelerated conditions, the key impurity ET-701 does not increase significantly, and there is no tendency to increase in the water content of the samples. It is demonstrated that the stability of sample under accelerated conditions and long-term conditions can be significantly improved by using a specific ratio of glucose and dextran 40 as the excipients.

What is claimed is:

1. A lyophilized composition, comprising trabectedin and a first excipient, and a second excipient, wherein the first excipient is one or more selected from the group consisting of glucose, fructose, galactose, sorbitol, mannitol, glycerol, and lactitol, and the second excipient is one or more selected from the group consisting of albumin, dextran, hydroxyethyl starch, sodium carboxymethyl cellulose, hydroxypropyl beta cyclodextrin, maltodextrin, and polyethylene glycol.

2. The composition according to claim 1, wherein the first excipient is glucose, and wherein the second excipient is selected from the group consisting of albumin, dextran, hydroxyethyl starch, sodium carboxymethyl cellulose, and hydroxypropyl beta cyclodextrin.

3. The composition according to claim 1, wherein the first excipient is sorbitol, and wherein the second excipient is selected from the group consisting of albumin, dextran, hydroxyethyl starch, sodium carboxymethyl cellulose, and hydroxypropyl beta cyclodextrin.

4. The composition according to claim 1, wherein the weight ratio of trabectedin to the first excipient is 1:10 to 1:2000.

5. The composition according to claim 1, wherein the weight ratio of trabectedin to the second excipient is 1:10 to 1:1000.

6. The composition according to claim 2, wherein the first excipient is glucose, and the second excipient is dextran.

7. The composition according to claim 6, wherein the composition has a weight ratio of glucose to dextran of 1:1 to 10:1.

8. The composition according to claim 6, wherein the glucose is present in an amount of 2-15% by weight, relative to the total weight of the composition.

9. The composition according to claim 6, wherein the dextran is present in an amount of 1-10% by weight, relative to the total weight of the composition.

10. The composition according to claim 1, wherein the composition further comprises a buffer salt selected from the group consisting of potassium dihydrogen phosphate, sodium dihydrogen phosphate, potassium citrate, and sodium citrate, and has a weight ratio of trabectedin to the buffer salt of 1:10 to 1:100.

11. The composition according to claim 1, wherein the lyophilized formulation is prepared from a solution with pH 3-5 before lyophilization.

12. An injectable pharmaceutical composition of trabectedin obtained by a process comprising reconstituting the lyophilized formulation according to claim 11.

13. The composition according to claim 12, further comprising at least one buffer, wherein the buffer is selected from the group consisting of phosphate buffer, lactate buffer, acetate buffer, and citrate buffer.

14. A preparation method for the lyophilized composition according to claim 1, comprising:
  1) dissolving trabectedin in an acidic buffer salt solution comprising an acid and a buffer salt to obtain a buffer solution of trabectedin, wherein the acid is phosphoric acid, and the buffer salt is potassium dihydrogen phosphate;
  2) dissolving the first excipient and the second excipient in a buffer salt solution to obtain a second buffer solution having a pH, and adjusting the pH of the second buffer solution to a set value;
  3) mixing the buffer solution of trabectedin of step 1) with the second buffer solution of step 2) to obtain a mixed solution having a pH, and then adjusting the pH of the mixed solution to a set value; and
  4) lyophilizing the mixed solution of step (3) to thereby obtain the lyophilized composition.

15. A lyophilized pharmaceutical composition, comprising trabectedin, glucose, and dextran, wherein the composition has a weight ratio of glucose to dextran of 1:1 to 1.5:1.

16. An injectable pharmaceutical composition of trabectedin obtained by a process comprising reconstituting the lyophilized formulation according to claim 15 with water for injection.

17. The lyophilized composition according to claim 15, further comprising a buffer salt selected from the group consisting of potassium dihydrogen phosphate, sodium dihydrogen phosphate, potassium citrate, and sodium citrate, and having a weight ratio of trabectedin to the buffer salt of 1:10 to 1:100.

18. The composition according to claim 15, wherein the lyophilized formulation is prepared from a solution with pH 3-5 before lyophilization.

* * * * *